United States Patent
Wang et al.

(10) Patent No.: US 9,833,135 B2
(45) Date of Patent: Dec. 5, 2017

(54) HIGH-RESOLUTION OPTICAL OPHTHALMOLOGY DETECTION APPARATUS AND OPERATING METHOD THEREOF

(71) Applicants: Crystalvue Medical Corporation, Taoyuan (TW); Sheng-Lung Huang, Taipei (TW)

(72) Inventors: William Wang, Taoyuan (TW); Chung-Ping Chuang, Taoyuan (TW); Meng-Shin Yen, Taipei (TW); Chung-Cheng Chou, Luzhu Township, Taoyuan County (TW); Sheng-Lung Huang, Taipei (TW); Kuang-Yu Hsu, Taipei (TW); Chien-Chung Tsai, Taipei (TW); Tuan-Shu Ho, Taipei (TW)

(73) Assignees: Crystalvue Medical Corporation, Taoyuan (TW); Sheng-Lung Huang, Taipei (TW)

( * ) Notice: Subject to any disclaimer, the term of this patent is extended or adjusted under 35 U.S.C. 154(b) by 0 days.

(21) Appl. No.: 14/485,388

(22) Filed: Sep. 12, 2014

(65) Prior Publication Data

US 2015/0077709 A1 Mar. 19, 2015

(30) Foreign Application Priority Data

Sep. 14, 2013 (TW) .............................. 102133382 A (51) Int. Cl.
- *A61B 3/12* (2006.01)
- *A61B 3/00* (2006.01)
- *A61B 3/14* (2006.01)

(52) U.S. Cl.
CPC .............. *A61B 3/0008* (2013.01); *A61B 3/12* (2013.01); *A61B 3/14* (2013.01)

(58) Field of Classification Search
CPC ......... A61B 3/1225; A61B 3/12; A61B 3/103; A61B 3/1015; A61B 3/0008; A61B 3/145;
(Continued)

(56) References Cited

U.S. PATENT DOCUMENTS

| | | | | |
|---|---|---|---|---|
| 6,018,413 A * | 1/2000 | Oka | ...................... | G02F 1/3501 359/326 |
| 7,229,435 B2 * | 6/2007 | Nakamura | .......... | A61F 9/00821 606/11 |

(Continued)

*Primary Examiner* — Bumsuk Won
*Assistant Examiner* — Henry Duong
(74) *Attorney, Agent, or Firm* — Muncy, Geissler, Olds & Lowe, P.C.

(57) ABSTRACT

An optical apparatus applied to ophthalmology detection is disclosed. The optical apparatus includes a first light source module, a second light source module, and an interference module. The first light source module is formed by a laser light source and lens units and used to emit a first light signal. The second light source module is formed by fiber units and lens units. The second light source module is coupled to the first light source module in series. The second light source module is used to receive a first light signal and emit a second light signal. The interference module is coupled to the second light source module and used to receive the second light signal and provide a first incident light and a second incident light to an object to be detected and a reference mirror respectively.

8 Claims, 5 Drawing Sheets

(58) Field of Classification Search
CPC ........... A61B 3/15; A61B 3/152; A61B 3/154; A61B 3/156; A61B 3/158; A61B 3/14; G02B 27/10; G02B 17/00; G02B 6/02095
USPC ................................................ 351/200, 221
See application file for complete search history.

(56) References Cited

U.S. PATENT DOCUMENTS

| | | | | |
|---|---|---|---|---|
| 8,873,065 | B2* | 10/2014 | Yoshida | A61B 3/102 |
| | | | | 356/479 |
| 9,119,571 | B2* | 9/2015 | Kato | A61B 3/1005 |
| 2011/0237999 | A1* | 9/2011 | Muller | A61F 9/008 |
| | | | | 604/20 |
| 2012/0170110 | A1* | 7/2012 | Lippey | G02B 27/48 |
| | | | | 359/327 |

* cited by examiner

HIGH-RESOLUTION OPTICAL OPHTHALMOLOGY DETECTION APPARATUS AND OPERATING METHOD THEREOF

BACKGROUND OF THE INVENTION

1. Field of the Invention

This invention relates to optical detection, especially to an optical apparatus and an optical apparatus operating method applied to ophthalmology detection providing effects of high power, large bandwidth, and high resolution.

2. Description of the Prior Art

In recent years, with the progress of optical detection technology, non-invasive optical detection apparatuses and methods are provided to detect the structure and composition of the tissue of the object to be detected; for example, it can be widely used in functional detection and medical diagnosis of human body. Especially, compared to other organs of human body, the eyes and their surrounding tissues have characteristics of high transparency and vulnerability to injury; therefore, the optical detection technology is suitable to be widely applied in ophthalmology detection apparatuses, such as an optometry machine, a tonometer, a fundus Camera, a corneal thickness meter, and an optical tomography scanner.

However, in practical applications, when the conventional optical ophthalmology detection apparatus is used to emit incident light is emitted to the tissues in the eyes, the different tissues may have different optical characteristics (e.g., reflection, scattering, refraction, or absorption), and the conventional optical ophthalmology detection apparatus may obtain detection results having poor resolution or even misjudgments.

Therefore, the invention provides an optical apparatus and an operating method thereof to solve the above-mentioned problems.

SUMMARY OF THE INVENTION

An embodiment of the invention is an optical apparatus. In this embodiment, the optical apparatus is applied to ophthalmology detection. The optical apparatus includes a first light source module, a second light source module, and an interference module. The first light source module is formed by a laser light source and lens units and used to emit a first light signal. The second light source module is formed by fiber units and lens units. The second light source module is coupled to the first light source module in series. The second light source module is used to receive the first light signal and emit a second light signal. The interference module is coupled to the second light source module and used to receive the second light signal and provide a first incident light and a second incident light to an object to be detected and a reference mirror respectively.

In an embodiment, the interference module includes an interference optical path for generating the first incident light and the second incident light according to the second light signal.

In an embodiment, the fiber units of the second light source module include a multi-mode fiber for generating the second light signal according to the first light signal.

In an embodiment, a core of the multi-mode fiber has a diameter of 100~600 um, and the first incident light provided by the interference module to the object to be detected has a central frequency of 700~1100 nm, a bandwidth wider than 20 nm, and an axial resolution smaller than 20 um.

In an embodiment, the reference mirror has a flat surface or a curved surface.

In an embodiment, the optical apparatus further includes a switching module. The switching module is coupled to the second light source module and another second light source module and the switching module is used for selectively switching to the second light source module or the another second light source module to generate the second light signal.

Another embodiment of the invention is an optical apparatus operating method. In this embodiment, the optical apparatus operating method is used to operate an optical apparatus applied to ophthalmology detection. The optical apparatus includes a first light source module, a second light source module, and an interference module. The first light source module includes a laser light source and lens units, the second light source module includes fiber units and lens units. The second light source module is coupled to the first light source module in series. The interference module is coupled to the second light source module. The method includes steps of: (a) the first light source module emitting a first light signal; (b) the second light source module receiving the first light signal and emitting a second light signal; and(c) the interference module receiving the second light signal and providing a first incident light and a second incident light to an object to be detected and a reference mirror respectively.

Compared to the prior art, the optical apparatus and the operating method thereof in the invention have many advantages of:

(1) using special-designed laser light source to achieve effects of high power output and optimal central bandwidth;

(2) using the special-designed light source modules cooperated with optical interference detection and matched special optical path design to effectively increase the signal-noise ratio (SNR) of system, so that the optical apparatus and the operating method thereof in the invention can be used to provide high-resolution longitudinal analysis of the eye tissue (e.g., cornea);

(3) using the switching module to switch the core mode and the cladding mode of the fiber unit in a rotational way or a moving way to provide different detection functions;

(4) using the curved surface reference mirror to replace the conventional flat surface reference mirror to increase the iris size and the signal-noise ratio (SNR).

The advantage and spirit of the invention may be understood by the following detailed descriptions together with the appended drawings.

DETAILED DESCRIPTION OF THE INVENTION

A preferred embodiment of the invention is an optical apparatus. In this embodiment, the optical apparatus can be an optical ophthalmology detection apparatus, but not limited to this.

Figure 1:
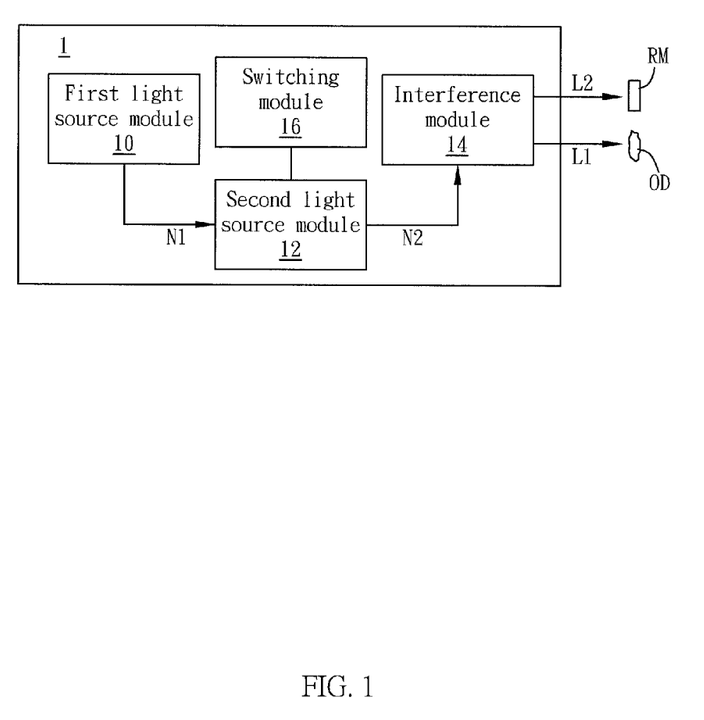
FIG. 1 illustrates a functional block diagram of the optical apparatus in an embodiment of the invention.

Please refer to FIG. 1. FIG. 1 illustrates a functional block diagram of the optical apparatus in this embodiment. As shown in FIG. 1, the optical apparatus 1 includes a first light source module 10, a second light source module 12, an interference module 14, and a switching module 16. Wherein, the second light source module 12 and the first light source module 10 are coupled in series. The interference module 14 is coupled to the second light source module 12. The switching module 16 is coupled to the second light source module 12.

In this embodiment, the first light source module 10 includes a laser light source and lens units. The first light source module 10 is used to emit a first light signal N1. In some cases, the first light source module 10 can also include fiber units, but not limited to this. The second light source module 12 includes fiber units and lens units. The second light source module 12 is used to receive the first light signal N1 from the first light source module 10 and emit a second light signal N2. The interference module 14 is used to receive the second light signal N2 from the second light source module 12 and provide a first incident light L1 and a second incident light L2 to an object OD to be detected and a reference mirror RM respectively.

Figure 2:
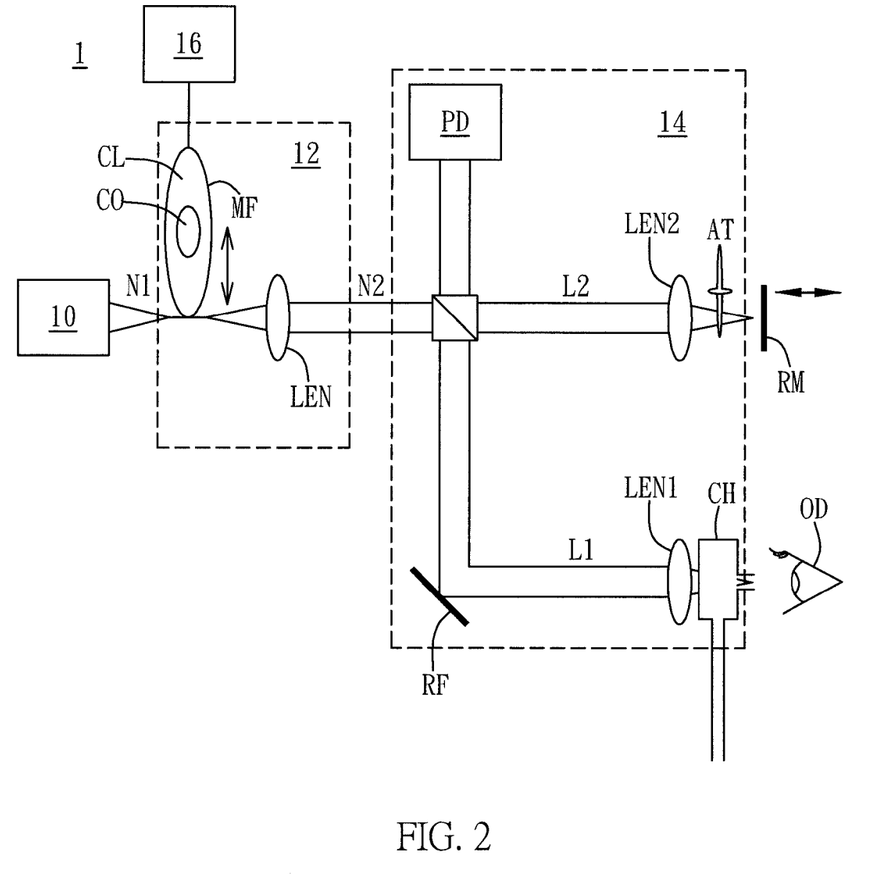
FIG. 2 illustrates an embodiment of the optical apparatus of FIG. 1 applied in an intraocular pressure measurement structure.

Please refer to FIG. 2. FIG. 2 illustrates an embodiment of the optical apparatus 1 of FIG. 1 applied in an intraocular pressure measurement structure. As shown in FIG. 2, the first light source module 10 and the second light source module 12 include different fiber units and lens units. It should be noticed that the fiber units of the second light source module 12 can include a collimating lens LEN and a multi-mode fiber MF used to generate the second light signal N2 according to the first light signal N1. In this embodiment, the multi-mode fiber MF includes a core CO and a cladding CL; the core CO of the multi-mode fiber MF used in the second light source module 12 can have a diameter of 100~600 um (e.g., 200 um), but not limited to this. The switching module 16 can be used to switch the multi-mode fiber MF of the second light source module 12 to a core mode or a cladding mode by moving the multi-mode fiber MF of the second light source module 12 to generate the second light signal N2, wherein the multi-mode fiber MF receives the first light signal Ni from the first light source module 10. When the witching module 16 switches the multi-mode fiber MF of the second light source module 12 to the core mode, the switching module 16 will move the multi-mode fiber MF of the second light source module 12, so that the first light signal N1 from the first light source module 10 can enter the core CO of the multi-mode fiber MF and be transmitted through the core CO of the multi-mode fiber MF to generate the second light signal N2; when the witching module 16 switches the multi-mode fiber MF of the second light source module 12 to the cladding mode, the switching module 16 will move the multi-mode fiber MF of the second light source module 12 again, so that the first light signal N1 from the first light source module 10 can enter the cladding CL of the multi-mode fiber MF and be transmitted through the cladding CL of the multi-mode fiber MF to generate the second light signal N2. In other words, the switching module 16 can control the multi-mode fiber MF of the second light source module 12 to be operated in the core mode or the cladding mode by moving the multi-mode fiber MF of the second light source module 12. This will also affect the central frequency, the bandwidth, and the axial resolution of the first incident light L1 that the interference module 14 provides to the object OD to be detected (e.g., corneal tissue).

In this embodiment, the interference module 14 can have an interference optical path (e.g., Michelson interference optical path, but not limited to this) used to receive the second light signal N2 from the multi-mode fiber MF of the second light source module 12 and generate the first incident light L1 and the second incident light L2 according to the second light signal N2. As shown in FIG. 2, the interference module 14 can include a light splitting unit K, a reflection unit RF, a light detection unit PD, lens units LEN1~LEN2, an attenuation unit AT, and a chamber CH.

The second light signal N2 from the multi-mode fiber MF of the second light source module 12 are split into the first incident light L1 and the second incident light L2 by the light splitting unit K. Then, the first incident light L1 will be reflected by the reflection unit RF and the reflected first incident light L1 will be emitted through the lens unit LEN1 and the chamber CH and then emitted toward the object OD to be detected; the second incident light L2 will be emitted through the lens unit LEN2 and the attenuation unit AT and then emitted toward the reference mirror RM. The light detection unit PD is used to receive a first reflected light formed by the object OD to be detected reflecting the first incident light L1 and receive a second reflected light formed by the reference mirror RM reflecting the second incident light L2 to obtain a measurement result according to the first reflected light and the second reflected light.

It should be noticed that the first incident light L1 that the interference module 14 provides to the object OD to be detected (e.g., corneal tissue) can have a central frequency of 700~1100 nm (e.g., 1030 nm), a bandwidth wider than 20 nm (e.g., 45 nm), and an axial resolution smaller than 20 um (e.g., 10 um), but not limited to this.

In fact, the fiber units of the second light source module 12 can include a single-mode fiber and a multi-mode fiber, and the optical apparatus 1 can further include a switching module coupled to the second light source module 12. The multi-mode fiber has many advantages such as: large bandwidth, high resolution, large area, good OCT effect.

Figure 3A:
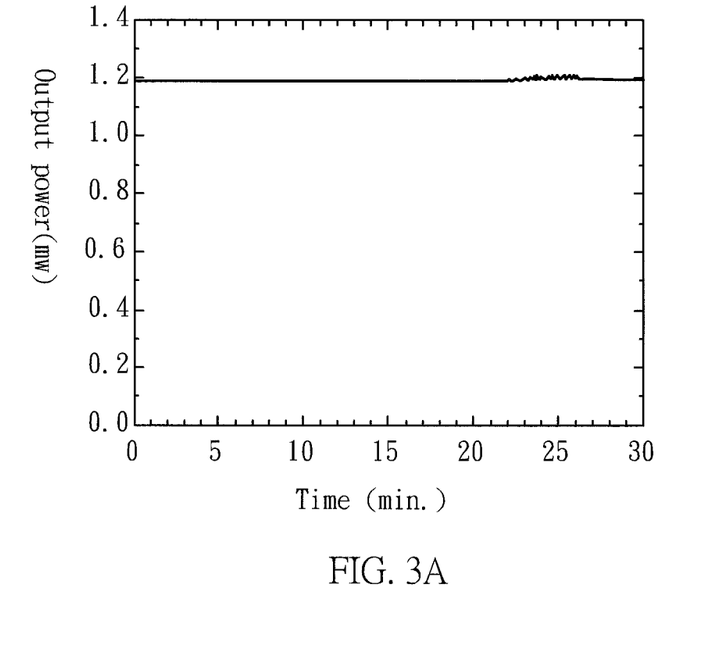
FIG. 3A and FIG. 3B illustrate experimental results of the output power and bandwidth obtained according to the optical apparatus respectively.
Figure 3B:
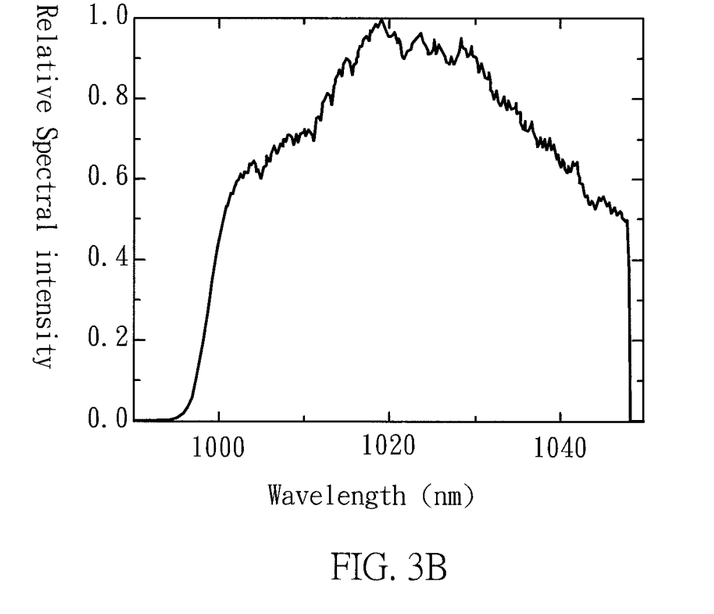

Please FIG. 3A and FIG. 3B. FIG. 3A and FIG. 3B illustrate experimental results of the output power and bandwidth obtained according to the optical apparatus respectively. As shown in FIG. 3A and FIG. 3B, the optical apparatus of the invention can achieve high output power (1.2 MW) and large bandwidth (47 nm).

In practical applications, the switching module 16 can be coupled to a plurality of second light source modules 12 and used for selectively switching to one of the plurality of second light source modules 12 to generate the second light signal N2, but not limited to this.

In practical applications, the switching module 16 can control the multi-mode fiber MF of the second light source module 12 to be operated in the core mode or the cladding mode. This will also affect the central frequency, the bandwidth, and the axial resolution of the first incident light Ll that the interference module 14 provides to the object OD to be detected (e.g., corneal tissue).

For example, when the switching module 16 controls the multi-mode fiber MF of the second light source module 12 to be operated in the core mode, the first incident light L1 that the interference module 14 provides to the object OD to be detected (e.g., corneal tissue) can have the central frequency of 1030 nm, the bandwidth of 19 nm, and the axial resolution of 22 um; when the switching module 16 controls the multi-mode fiber MF of the second light source module 12 to be operated in the cladding mode, the first incident light L1 that the interference module 14 provides to the object OD to be detected (e.g., corneal tissue) can have the central frequency of 1030 nm, the bandwidth of 47 nm, and the axial resolution of 9.1 um.

According to the above-mentioned measurement results, it can be found that the central frequency of the first incident light L1 in the cladding mode is equal to that in the core mode, but the bandwidth of the first incident light L1 in the cladding mode is obviously larger than that in the core mode, and the axial resolution of the first incident light L1 in the cladding mode is obviously better (smaller value) than that in the core mode. Therefore, the user can use the switching module 16 to control the multi-mode fiber MF of the second light source module 12 to be operated in the core mode or the cladding mode based on practical needs.

Figure 4:
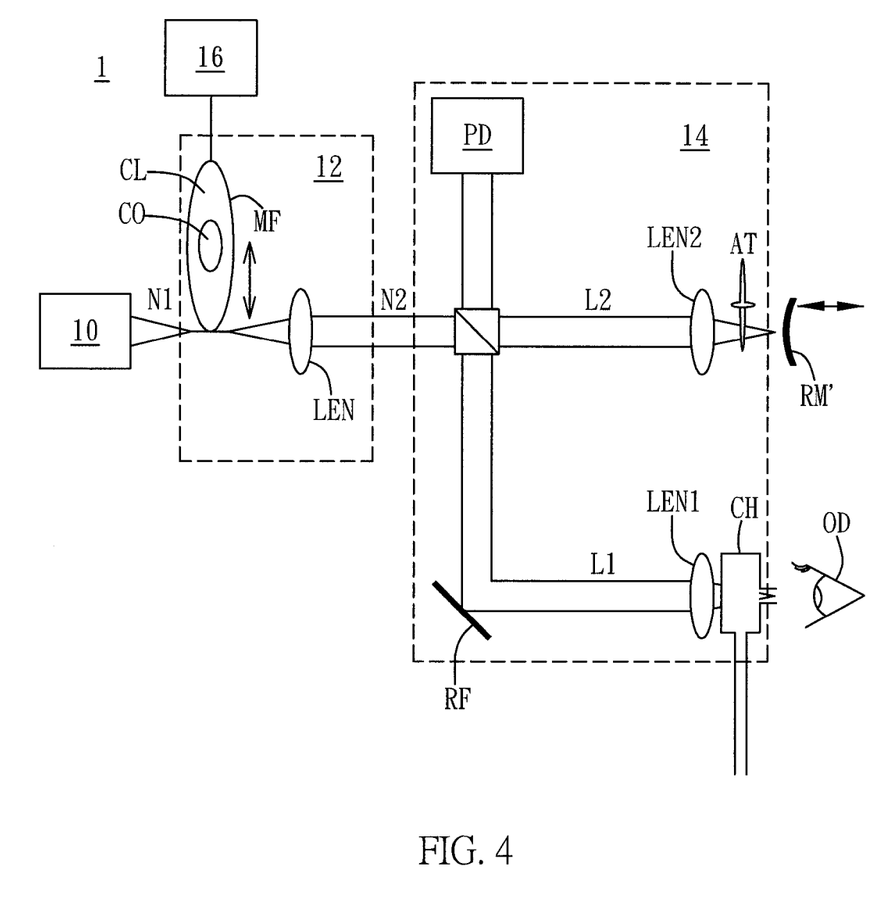
FIG. 4 illustrates another embodiment of the optical apparatus of FIG. 1 applied in an intraocular pressure measurement structure.

Please refer to FIG. 4. FIG. 4 illustrates another embodiment of the optical apparatus of FIG. 1 applied in an intraocular pressure measurement structure. Comparing FIG. 4 with FIG. 2, in this embodiment, a curved-surface reference mirror RM' of FIG. 4 is used to replace the flat-surface reference mirror RM of FIG. 2 to obtain larger iris size and better signal-noise ratio (SNR).

Another embodiment of the invention is an optical apparatus operating method. In this embodiment, the optical apparatus operating method is applied to ophthalmology detection. The optical apparatus includes a first light source module, a second light source module, and an interference module. The first light source module includes a laser light source and lens units; the second light source module includes fiber units and lens units. The second light source module is coupled to the first light source module in series. The interference module is coupled to the second light source module.

Figure 5:
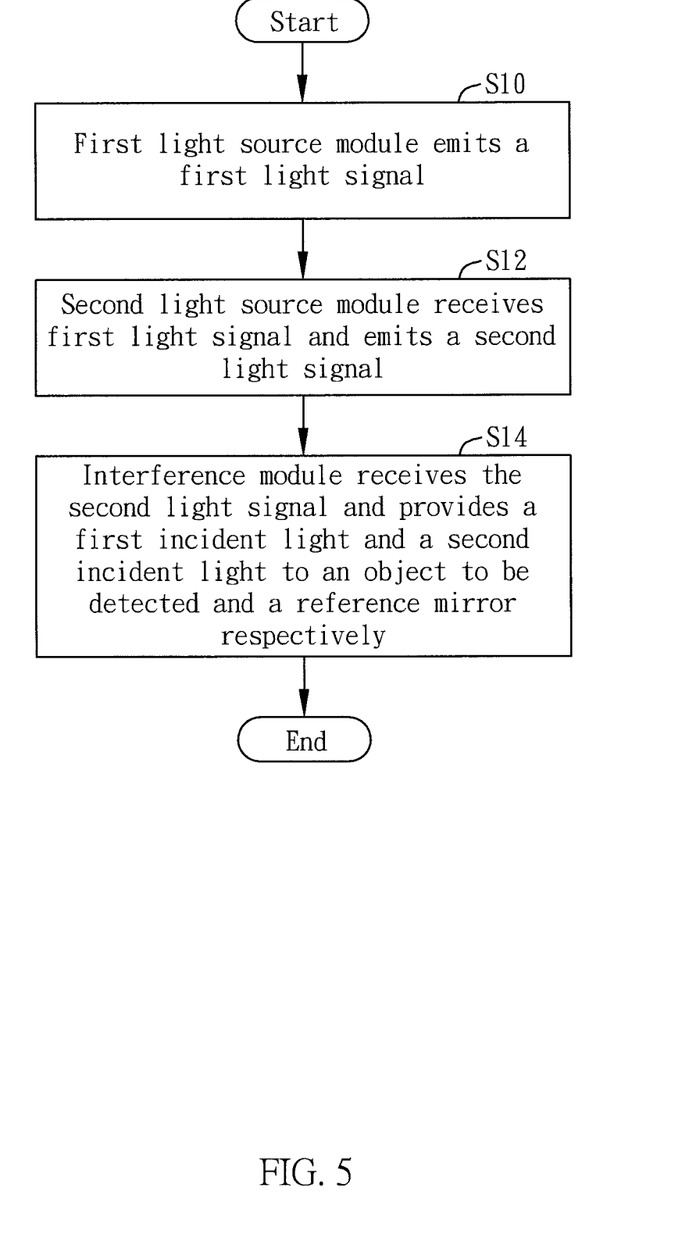
FIG. 5 illustrates a flowchart of the optical apparatus operating method in another embodiment of the invention.

Please refer to FIG. 5. FIG. 5 illustrates a flowchart of the optical apparatus operating method in this embodiment. As shown in FIG. 5, in the step S10, the first light source module emits a first light signal; in the step S12, the second light source module receives the first light signal and emits a second light signal; in the step S14, the interference module receives the second light signal and provides a first incident light and a second incident light to an object to be detected and a reference mirror respectively.

In practical applications, the fiber units of the second light source module include a multi-mode fiber. In the step S12, the method can selectively switch to one of the plurality of second light source modules to generate the second light signal. the method can also switch the multi-mode fiber of the second light source module to be operated in a core mode or in a cladding mode in a rotational way or a moving way to generate the second light signal, wherein the multi-mode fiber receives the first light signal from the first light source module. The reference mirror can have a flat surface or a curved surface. In the step S14, the interference module can include an interference optical path used for generating the first incident light and the second incident light according to the second light signal. The first incident light provided by the interference module to the object to be detected can have a central frequency of 700~1100 nm (e.g., 1030 nm), a bandwidth wider than 20 nm (e.g., 45 nm), and an axial resolution smaller than 20 um (e.g., 10 um), but not limited to this.

Compared to the prior art, the optical apparatus and the operating method thereof in the invention have many advantages of:

(1) using special-designed laser light source to achieve effects of high power output and optimal central bandwidth;

(2) using the special-designed light source modules cooperated with optical interference detection and matched special optical path design to effectively increase the signal-noise ratio (SNR) of system, so that the optical apparatus and the operating method thereof in the invention can be used to provide high-resolution longitudinal analysis of the eye tissue (e.g., cornea);

(3) using the switching module to switch the core mode and the cladding mode of the fiber unit in a rotational way or a moving way to provide different detection functions;

(4) using the curved surface reference mirror to replace the conventional flat surface reference mirror to increase the iris size and the signal-noise ratio (SNR).

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical apparatus, comprising:
   a first light source module, comprising a laser light source, and lens units, for emitting a first light signal;
   a second light source module, comprising fiber units and lens units and directly coupled to the first light source module in series, for receiving the first light signal and emitting a second light signal, wherein the fiber units of the second light source module comprise a multi-mode fiber for generating the second light signal according to the first light signal; and
   an interference module, coupled to the second light source module, for receiving the second light signal and providing a first incident light and a second incident light to an object to be detected and a reference mirror having a curved surface respectively;
   wherein the optical apparatus further comprises:
   a switching module, coupled to the second light source module and configured to selectively switch the multi-mode fiber of the second light source module to a core mode or a cladding mode by moving the multi-mode fiber of the second light source module to control the multi-mode fiber of the second light source module to be operated in the core mode or the cladding mode to generate the second light signal, wherein a central frequency of the first incident light in the cladding mode is equal to the central frequency of the first incident light in the core mode, but a bandwidth of the first incident light in the cladding mode is larger than the bandwidth of the first incident light in the core mode, and an axial resolution of the first incident light in the cladding mode is better than the axial resolution of the first incident light in the core mode.

2. The optical apparatus of claim 1, wherein the interference module comprises an interference optical path for generating the first incident light and the second incident light according to the second light signal.

3. The optical apparatus of claim 1, wherein a core of the multi-mode fiber has a diameter of 100~600 um, and the first incident light provided by the interference module to the object to be detected has a central frequency of 700~1100 nm, a bandwidth wider than 20 nm, and an axial resolution smaller than 20 um.

4. The optical apparatus of claim 1, further comprising:
a switching module, coupled to the second light source module and another second light source module, for selectively switching to the second light source module or the another second light source module to generate the second light signal.

5. A method of operating an optical apparatus, the optical apparatus comprising a first light source module, a second light source module, and an interference module, the first light source module comprising a laser light source and lens units, the second light source module comprising fiber units and lens units, the second light source module being directly coupled to the first light source module in series, the interference module being coupled to the second light source module, the method comprising steps of:
(a) the first light source module emitting a first light signal;
(b) the second light source module receiving the first light signal and emitting a second light signal, wherein the fiber units of the second light source module comprise a multi-mode fiber for generating the second light signal according to the first light signal; and
(c) the interference module receiving the second light signal and providing a first incident light and a second incident light to an object to be detected and a reference mirror having a curved surface respectively;
wherein the optical apparatus further comprises a switching module, the switching module is coupled to the second light source module and configured to selectively switch the multi-mode fiber of the second light source module to a core mode or a cladding mode by moving the multi-mode fiber of the second light source module to control the multi-mode fiber of the second light source module to be operated in the core mode or the cladding mode to generate the second light signal, wherein a central frequency of the first incident light in the cladding mode is equal to the central frequency of the first incident light in the core mode, but a bandwidth of the first incident light in the cladding mode is larger than the bandwidth of the first incident light in the core mode, and an axial resolution of the first incident light in the cladding mode is better than the axial resolution of the first incident light in the core mode.

6. The method of claim 5, wherein the interference module comprises an interference optical path for generating the first incident light and the second incident light according to the second light signal.

7. The method of claim 5, wherein a core of the multi-mode fiber has a diameter of 100~600 um, the first incident light provided by the interference module to the object to be detected has a central frequency of 700~1100 nm, a bandwidth wider than 20 nm, and an axial resolution smaller than 20 um.

8. The method of claim 5, further comprising a step of:
selectively switching to the second light source module or another second light source module to generate the second light signal.

* * * * *